US007759393B2

(12) United States Patent
Joerger et al.

(10) Patent No.: US 7,759,393 B2
(45) Date of Patent: *Jul. 20, 2010

(54) BIO-DERIVED 1,3-PROPANEDIOL AND ITS CONJUGATE ESTERS AS NATURAL AND NON IRRITATING SOLVENTS FOR BIOMASS-DERIVED EXTRACTS, FRAGRANCE CONCENTRATES, AND OILS

(75) Inventors: Melissa Joerger, Newark, DE (US); Gyorgyi Fenyvesi, Wilmington, DE (US); Raja Hari Prasad R. Poladi, Bear, DE (US); Robert Miller, Wilmington, DE (US)

(73) Assignee: DuPont Tate & Lyle Bio Products Company, LLC, Wilmington, DE (US)

( * ) Notice: Subject to any disclaimer, the term of this patent is extended or adjusted under 35 U.S.C. 154(b) by 78 days.

This patent is subject to a terminal disclaimer.

(21) Appl. No.: 11/705,198

(22) Filed: Feb. 12, 2007

(65) Prior Publication Data
US 2007/0202126 A1 Aug. 30, 2007

Related U.S. Application Data

(60) Provisional application No. 60/772,471, filed on Feb. 10, 2006, provisional application No. 60/772,194, filed on Feb. 10, 2006, provisional application No. 60/772,193, filed on Feb. 10, 2006, provisional application No. 60/772,111, filed on Feb. 10, 2006, provisional application No. 60/772,120, filed on Feb. 10, 2006, provisional application No. 60/772,110, filed on Feb. 10, 2006, provisional application No. 60/772,112, filed on Feb. 10, 2006, provisional application No. 60/846,948, filed on Sep. 25, 2006, provisional application No. 60/853,920, filed on Oct. 24, 2006, provisional application No. 60/859,264, filed on Nov. 15, 2006, provisional application No. 60/872,705, filed on Dec. 4, 2006, provisional application No. 60/880,824, filed on Jan. 17, 2007.

(51) Int. Cl.
*A61K 31/22* (2006.01)
*A61K 31/23* (2006.01)
*A61K 31/045* (2006.01)
*A61K 35/60* (2006.01)
*A61K 35/20* (2006.01)
*A61K 36/00* (2006.01)

(52) U.S. Cl. .................. 514/546; 514/552; 514/724; 424/520; 424/535; 424/725

(58) Field of Classification Search .................. 514/546, 514/552, 724; 424/520, 535, 725
See application file for complete search history.

(56) References Cited

U.S. PATENT DOCUMENTS 4,897,220 A * 1/1990 Trieselt et al. ............... 510/360
5,633,362 A 5/1997 Nagarajan et al.
5,686,276 A 11/1997 Laffend et al.
5,716,604 A 2/1998 Coe et al.
5,821,092 A 10/1998 Nagarajan et al.
6,025,184 A 2/2000 Laffend et al.
6,123,932 A 9/2000 Guskey et al.
6,136,576 A 10/2000 Diaz-Torres et al.
6,174,521 B1 1/2001 Li et al.
6,358,716 B1 3/2002 Bulthuis et al.
6,361,983 B1 * 3/2002 Ames .......................... 435/158
6,406,895 B1 6/2002 Defretin et al.
6,428,767 B1 8/2002 Burch et al.
6,479,716 B2 11/2002 Hilaly et al.
6,555,700 B1 4/2003 Horrobin et al.
6,576,340 B1 6/2003 Sun et al.
6,726,887 B1 4/2004 Sugarman
7,098,368 B2 8/2006 Seapan et al.
2003/0082756 A1 * 5/2003 Burch et al. ................. 435/158
2004/0105899 A1 6/2004 Dowdle et al.
2005/0009721 A1 1/2005 Delplancke et al.
2005/0020805 A1 1/2005 Sunkara et al.
2005/0069997 A1 3/2005 Adkesson et al.
2005/0154114 A1 7/2005 Hale (Continued)

FOREIGN PATENT DOCUMENTS

JP 55050859 4/1980

(Continued)

OTHER PUBLICATIONS

Merriam-Webster Online Dictionary [online], Merriam-Webster Online, 2008 [retrieved on Jul. 28, 2008]. Retrieved from the Internet: <URL: http://www.merriam-webster.com/dictionary/ore.*

(Continued)

Primary Examiner—Raymond J Henley, III
(74) Attorney, Agent, or Firm—McCarter and English

(57) ABSTRACT

Compositions containing 1,3-propanediol and an extraction product are provided, and the 1,3-propanediol in the composition is biologically derived. Also provided are processes for extracting an extract from a source. These processes include providing an ester of 1,3-propanediol and mixing the 1,3-propanediol ester with the source. This serves to extract the extract from the source into the ester. The processes also include separating the source from the ester and extract. Also provided are compositions containing an ester of 1,3-propanediol and an extraction product. In these compositions, the ester can have at least 3% biobased carbon.

27 Claims, No Drawings

U.S. PATENT DOCUMENTS

| | | | |
|---|---|---|---|
| 2006/0035808 | A1 | 2/2006 | Ahmed et al. |
| 2006/0110810 | A1 | 5/2006 | Rajgarhia et al. |
| 2006/0148053 | A1 | 7/2006 | Emptage et al. |
| 2007/0193960 | A1 | 8/2007 | Frank et al. |

FOREIGN PATENT DOCUMENTS

| | | |
|---|---|---|
| JP | 5221821 | 8/1993 |
| JP | 2002138069 | 5/2002 |

OTHER PUBLICATIONS

Galinksy et al ["Basic Pharmacokinetics and Pharmacodynamics." in: Remington: The Science and Practice of Pharmacy (Baltimore, Lippincott Williams & Wilkins, 2006), p. 1171.].*

Pesticide Action Network (PAN) Pesticides Database [online], www.pesticideinfo.org, 2008 [retrieved on Jul. 30, 2008]. Retrieved from the Internet: <URL: http://www.pesticideinfo.org/Detail_Chemical.jsp?Rec_Id=PC34262.*

"Industrial Bioproducts: Today and Tomorrow" (Paster et al.) Prepared by Energetics, Inc. for the US Department of Energy, Jul. 2003, See p. 1 and 2, Table 1-1 and 1-6.

Chen, et al. "Cyclization During Polyesterifications: Isolation Of An 18-Member Ring Compound from Reaction of Phthalic Anhydride With 2,2-Dimethyl-1,3-Propanediol"; Journal of Applied Polymer Science, 1990, vol. 41, Issue 9-10, pp. 2517-2520.

Fung, et al. "Evolution of Carbon Sinks in a Changing Climate"; PNAS, Aug. 9, 2005, vol. 12, No. 32; pp. 11201-11206.

Jabrane, et al., "Study of the Thermal Behaviour of 1,3-Propanediol and its Aqueous Solutions"; Thermochimica Acta 311 (1998); pp. 121-127.

* cited by examiner

BIO-DERIVED 1,3-PROPANEDIOL AND ITS CONJUGATE ESTERS AS NATURAL AND NON IRRITATING SOLVENTS FOR BIOMASS-DERIVED EXTRACTS, FRAGRANCE CONCENTRATES, AND OILS

CROSS REFERENCE TO RELATED APPLICATIONS

The present application claims the benefit of U.S. Provisional Application Ser. No. 60/772,471, filed Feb. 10, 2006; U.S. Provisional Application No. 60/772,194, filed Feb. 10, 2006, U.S. Provisional Application No. 60/772,193, filed Feb. 10, 2006, U.S. Provisional Application No. 60/772,111, filed Feb. 10, 2006, U.S. Provisional Application No. 60/772,120, filed Feb. 10, 2006, U.S. Provisional Application No. 60/772,110, filed Feb. 10, 2006, U.S. Provisional Application No. 60/772,112, filed Feb. 10, 2006, U.S. Provisional Application No. 60/846,948, filed Sep. 25, 2006, U.S. Provisional Application No. 60/853,920, filed Oct. 24, 2006, U.S. Provisional Application No. 60/859,264, filed Nov. 15, 2006, U.S. Provisional Application No. 60/872,705, filed Dec. 4, 2006 and U.S. Provisional Application No. 60/880,824, filed Jan. 17, 2007, the disclosures of which are expressly incorporated herein by reference in their entireties.

FIELD OF THE INVENTION

The invention relates to compositions comprising solvents and extracts, and methods of extracting compounds from materials using solvents.

BACKGROUND OF THE INVENTION

Consumers and manufacturers are increasingly concerned with the environmental impact of all products. The effort towards environmental impact awareness is a universal concern, recognized by government agencies. The Kyoto Protocol amendment to the United Nations Framework Convention on Climate Change (UNFCCC) currently signed by 156 nations is one example of a global effort to favor safer environmental manufacturing over cost and efficiency. Especially when applied to goods like, personal care, cosmetics, therapeutics and cosmeceuticals, consumers are increasingly selective about the origins of the products they purchase. The 2004 Co-operative Bank's annual Ethical Consumerism Report (www.co-operativebank.co.uk) disclosed a 30.3% increase in consumer spending on ethical retail products (a general classification for environmental safe, organic and fair trade goods) between 2003 and 2004, while total consumer spending during the same period rose only 3.7%.

One of the single greatest environmental concerns to consumers is the global warming effect and greenhouse gases that contribute to the effect. Greenhouse gases are gases that allow sunlight to enter the atmosphere freely. When sunlight strikes the Earth's surface, some of it is reflected back towards space as infrared radiation. Greenhouse gases absorb this infrared radiation and trap the heat in the atmosphere. Over time, the amount of energy sent from the sun to the Earth's surface should be about the same as the amount of energy radiated back into space, leaving the temperature of the Earth's surface roughly constant. However, increasing the quantity of greenhouse gases above the quantity that existed before the rise of human industrialization is thought to increase the retained heat on the Earth's surface and produce the global warming observed in the last two centuries.

Carbon dioxide is singled out as the largest component of the collection of greenhouse gases in the atmosphere. The level of atmospheric carbon dioxide has increased 50% in the last two hundred years. Any further addition of carbon dioxide to the atmosphere is thought to further shift the effect of greenhouse gases from stabilization of global temperatures to that of heating. Consumers and environmental protection groups alike have identified industrial release of carbon into the atmosphere as the source of carbon causing the greenhouse effect. Only organic products composed of carbon molecules from renewably based sources such as plant sugars and starches and ultimately atmospheric carbon are considered to not further contribute to the greenhouse effect, when compared to the same organic molecules that are petroleum or fossil fuel based.

In addition to adding carbon dioxide to the atmosphere, current methods of industrial production of propanediols produce contaminants and waste products that include among them sulfuric acid, hydrochloric acid, hydrofluoric acid, phosphoric acid, tartaric acid, acetic acids, Alkali metals, alkaline earth metals, transitional metals and heavy metals, including Iron, cobalt, nickel, copper, silver, molybdenum, tungsten, vanadium, chromium, rhodium, palladium, osmium, iridium, rubidium, and platinum (U.S. Pat. Nos. 2,434,110, 5,034,134, 5,334,778, and 5,10,036).

There is a need for all manufactures to provide products reduced environmental impacts, and to especially consider the carbon load on the atmosphere. There is also an environmental advantage for manufacturers to provide products of renewably based sources. Further, there is a need for a proven solvent which is produced with no or little increase to the present carbon-dioxide level in the environment.

Published U.S. Patent Application No. 2005/0069997 discloses a process for purifying 1,3-propanediol from the fermentation broth of a cultured $E.$ $coli$ that has been bioengineered to synthesize 1,3-propanediol from sugar. The basic process entails filtration, ion exchange and distillation of the fermentation broth product stream, preferably including chemical reduction of the product during the distillation procedure. Also provided are highly purified compositions of 1,3-propanediol.

Personal care, animal care, cosmetic, therapeutic, pharmaceutic, nutraceutic, aromatherapy, fragrance and cosmeceutic formulations benefit from glycols in the compositions as, for example, surfactants, humectants, solvents, neutralizers, emulsifiers, preservatives and/or fragrance enhancers and fixatives. Typically the glycol component in personal care applications include propylene glycol, 1,3-butylene glycol, or 2-methyl-1,3-propanediol. Because of production costs and relative low purity, conventional 1,3-propanediol, though exhibiting properties equal to if not better than the aforementioned glycols, generally is not used in such compositions.

Moreover, in the context of personal care, animal care, cosmetic, therapeutic, pharmaceutic, nutraceutic, aromatherapy, fragrance and cosmeceutic formulations incorporating a botanical, vegetal, protein/peptide, marine, algae or milk extract, or fragrance concentrate or oil, consumers pay attention to the quality and environmental impact of the product. Currently, botanical, vegetal, protein/peptide, marine, algae and milk extracts, and fragrance concentrates utilize chemical solvents, such as propylene glycol, 2-methyl-1,3-propanediol, butylene glycol, dipropylene glycol, synthetic glycerin, and ethanol, for the extraction process. In many cases these chemical solvents are used in combination with each other. Despite the fact these chemicals are suitable solvents, they have an intrinsic disadvantage because they represent a petroleum-based component of an otherwise "all natural" product. Additionally, safety assessments of these solvents provide evidence that they can cause skin irritation. (Cosmetic Ingredient Review Expert Panel (1994) Final Report on the Safety Assessment of Propylene Glycol and Polypropylene Glycols. J. Am. College Toxicol., 13(6):437-491).

Essential oils extracted from plants are widely used cosmetic and personal care formulations. Colors extracted from plants are used in the food and non-food-industry. Medicinal plant extractions are being used for the treatment various disorders. Though several methods can be used for extraction of flavors, fragrances, colors, and active ingredients, solvent extraction is one of widely used method. Selective extraction of required ingredients, stability of the extracted ingredients, and separation of ingredients from unwanted solvents are key factors for extraction. When volatile solvents such as ethanol used for extraction of active ingredients, they need to be removed before using the ingredients in formulations. When solvents are removed some of the active ingredients may not be stable and decompose.

SUMMARY OF THE INVENTION

Compositions comprising 1,3-propanediol and an extraction product are provided, and the 1,3-propanediol in the composition is biologically derived. Also provided are processes for extracting an extract from a source. These processes comprise providing an ester of 1,3-propanediol and mixing the 1,3-propanediol ester with the source. This serves to extract the extract from the source into the ester. The processes also include separating the source from the ester and extract. Also provided are compositions comprising an ester of 1,3-propanediol and an extraction product. In these compositions, the ester can have at least 3% biobased carbon.

DETAILED DESCRIPTION

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Solvents for diluting and extracting natural extracts are often synthetic, petroleum based organic solvents. Botanical, vegetal, protein/peptide, marine, algae, and milk extracts, also known as an essential oils, are an attractive component in many compositions. These essential oils impart aromatics, active ingredients, and other functionalities such as hand-feel, softening, emoillency, healing, cooling, refreshing, antimicrobial, astringency, nail-strengthening, promotion of healthy skin tissue and hair, cleansing, stimulating, whitening, delivery of anti-oxidants and skin-soothing attributes to a product. Essential oils are the volatile oils of plant/vegetal, protein/peptide, lipid, marine, algae or milk materials that have been removed either by distillation or solvent extraction.

Biologically-derived 1,3-propanediol and its conjugate esters can be used as a solvent to extract essential oils and other extracts from extract sources. Bio-derived 1,3-propanediol and its conjugate esters can be used as a solvent system for botanical extracts and fragrance concentrates and oils at a 10% to approaching 100% concentration range.

Additionally, biologically-derived 1,3-propanediol and its conjugate esters can be used as a solvent to dilute or solubilize extracts in compositions. Biologically-derived 1,3-propanediol and its conjugate esters are unique as solvents in that they are naturally derived, and therefore attractive to consumers who avoid synthetic chemicals.

Biologically-derived 1,3-propanediol and its conjugate esters provide for non-irritating solvents for the extraction and dilution of botanicals, vegetal, protein/peptide, marine, algae, milk substrates or fragrance concentrates and oils. In an aspect of the invention the solvent is composed of all natural components, the term "all natural" as used herein refers to a product that is manufactured from ingredients that are natural occurring. Specifically, biologically derived 1,3-propanediol comprises non-petroleum based carbon.

The conjugate esters of biologically-derived 1,3-propanediol discussed herein include the mono and diesters of biologically derived 1,3-propanediol.

Biologically-derived 1,3-propanediol or its ester conjugates are employed as chemical solvents for extraction or diluent of a botanical extract or fragrance concentrate or oil. The process of extracting an extract from a source comprises: (a) providing 1,3-propanediol, an ester of 1,3-propanediol, or a mixture thereof; (b) mixing the 1,3-propanediol, the ester of 1,3-propanediol, or the mixture thereof with the source, which extracts the extract from the source into the ester; and (c) separating the source from the extract and 1,3-propanediol, the ester of 1,3-propanediol, or the mixture thereof.

The process of extraction involves use of a dried substrate such as plant material which is macerated with solvent. Maceration is the most common and economically important technique for extracting aromatics in the modern perfume industry. In this method, raw materials are submerged in a solvent that can dissolve the desired aromatic or other extract compounds. Maceration lasts between fractions of an hour to months. Maceration is often used to extract fragrant compounds from woody or fibrous materials, as well as animal sources. This technique is also useful to extract odorants that are too volatile for distillation or easily denatured by heat.

Alternatively the solvent can be percolated though the substrate material until sufficient soluble materials have leached from the biomass or substrate. The substrate debris is separated from the extract by straining, filtering, or centrifugation.

Another technique for extracting compounds from a raw material is supercritical fluid extraction. This technique uses low heat to reduce degradation of the extract compounds. Supercritical $CO_2$ can be used in this extraction technique.

Extraction can be performed in accordance with the invention by other extraction techniques as well, including distillation. Biologically-derived 1,3-propanediol and its conjugate esters can be used as solvents in distillation extractions. In this technique, commonly used to obtain aromatic compounds from plants, such as orange blossoms and roses, the raw material is heated and the fragrant compounds are recollected through condensation of the distilled vapor. Distillation methods include steam distillation, in which steam is used to drive out volatile fragrant compounds from plant material, leaving a condensate which is called a hydrosol. Distillation also includes dry or destructive distillation where the raw material is heated without a carrier solvent. In this case, biologically-derived 1,3-propanediol and its conjugate esters are used as a solvent to dilute the fragrant compounds after extraction.

In yet another method of extraction, known as expression, raw material is physically squeezed or compressed and the extruded oils are collected. This method is known as extraction and is most commonly performed to extract compounds from the peels of fruits in the citrus family, as these sources contain sufficient oils to make this method feasible. Enfleurage is another extraction method appropriate for use with biologically derived 1,3-propanediol, its conjugate esters, or mixtures thereof.

Biologically derived 1,3-propanediol and its conjugate esters are useful as a solvents for extractions, and as a component in compositions comprising botanical extracts. Botanical sources include, but are not limited to all plants, seeds, stems, roots, flowers, leaves, pollen, spices, and oils. One type of extract appropriate for extraction or dilution is the herbal extract.

An herbal extract is a liquid solution of herbs and solvent. The dried or fresh herbs are combined with solvent, then the solid matter is removed leaving only the oils of the herbs mixed with the solvent. This process is called extraction, and the process produces an herbal extract.

Herbal extracts are sold as dietary supplements and alternative medicine and commonly used for flavoring in baking, cooking or in beverages. They are also used in personal care products such as skin and hair products.

A small amount of the carbon dioxide in the atmosphere is radioactive. This 14C carbon dioxide is created when nitrogen is struck by an ultra-violet light produced neutron, causing the nitrogen to lose a proton and form carbon of molecular weight 14 which is immediately oxidized in carbon dioxide. This radioactive isotope represents a small but measurable fraction of atmospheric carbon. Atmospheric carbon dioxide is cycled by green plants to make organic molecules during the process known as photosynthesis. The cycle is completed when the green plants or other forms of life metabolize the organic molecules producing carbon dioxide which is released back to the atmosphere. Virtually all forms of life on Earth depend on this green plant production of organic molecule to produce the chemical energy that facilitates growth and reproduction. Therefore, the 14C that exists in the atmosphere becomes part of all life forms, and their biological products. These renewably based organic molecules that biodegrade to $CO_2$ do not contribute to global warming as there is no net increase of carbon emitted to the atmosphere. In contrast, fossil fuel based carbon does not have the signature radiocarbon ratio of atmospheric carbon dioxide.

Assessment of the renewably based carbon in a material can be performed through standard test methods. Using radiocarbon and isotope ratio mass spectrometry analysis, the biobased content of materials can be determined. ASTM International, formally known as the American Society for Testing and Materials, has established a standard method for assessing the biobased content of materials. The ASTM method is designated ASTM-D6866.

The application of ASTM-D6866 to derive a "biobased content" is built on the same concepts as radiocarbon dating, but without use of the age equations. The analysis is performed by deriving a ratio of the amount of radiocarbon (14C) in an unknown sample to that of a modern reference standard. The ratio is reported as a percentage with the units "pMC" (percent modern carbon). If the material being analyzed is a mixture of present day radiocarbon and fossil carbon (containing no radiocarbon), then the pMC value obtained correlates directly to the amount of Biomass material present in the sample.

The modern reference standard used in radiocarbon dating is a NIST (National Institute of Standards and Technology) standard with a known radiocarbon content equivalent approximately to the year AD 1950. AD 1950 was chosen since it represented a time prior to thermo-nuclear weapons testing which introduced large amounts of excess radiocarbon into the atmosphere with each explosion (termed "bomb carbon"). The AD 1950 reference represents 100 pMC.

"Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. It's gradually decreased over time with today's value being near 107.5 pMC. This means that a fresh biomass material such as corn could give a radiocarbon signature near 107.5 pMC.

Combining fossil carbon with present day carbon into a material will result in a dilution of the present day pMC content. By presuming 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, it would give a radiocarbon signature near 54 pMC.

A biomass content result is derived by assigning 100% equal to 107.5 pMC and 0% equal to 0 pMC. In this regard, a sample measuring 99 pMC will give an equivalent biobased content result of 93%.

Assessment of the materials described herein were done in accordance with ASTM-D6866. The mean values quoted in this report encompasses an absolute range of 6% (plus and minus 3% on either side of the biobased content value) to account for variations in end-component radiocarbon signatures. It is presumed that all materials are present day or fossil in origin and that the desired result is the amount of biobased component "present" in the material, not the amount of biobased material "used" in the manufacturing process.

"Substantially purified," as used by applicants to describe the biologically-produced 1,3-propanediol produced by the process of the invention, denotes a composition comprising 1,3-propanediol having at least one of the following characteristics: 1) an ultraviolet absorption at 220 nm of less than about 0.200 and at 250 nm of less than about 0.075 and at 275 nm of less than about 0.075; or 2) a composition having L*a*b* "b*" color value of less than about 0.15 and an absorbance at 270 nm of less than about 0.075; or 3) a peroxide composition of less than about 10 ppm; or 4) a concentration of total organic impurities of less than about 400 ppm.

A "b*" value is the spectrophotometrically determined "Yellow Blue measurement as defined by the CIE L*a*b* measurement ASTM D6290. The abbreviation "AMS" refers to accelerator mass spectrometry.

The abbreviation "IRMS" refers to measurements of $CO_2$ by high precision stable isotope ratio mass spectrometry.

"Biologically produced" means organic compounds produced by one or more species or strains of living organisms, including particularly strains of bacteria, yeast, fungus and other microbes. "Bio-produced," "biologically-derived" and "biologically produced" are used synonymously herein. Such organic compounds are composed of carbon from atmospheric carbon dioxide converted to sugars and starches by green plants.

"Biologically-based" means that the organic compound is synthesized from biologically produced organic components. It is further contemplated that the synthesis process disclosed herein is capable of effectively synthesizing other monoesters and diesters from bio-produced alcohols other than 1,3-propanediol; particularly including ethylene glycol, diethylene glycol, triethylene glycol, -, dipropylene diol, tripropylene diol, 2-methyl 1,3-propanediol, neopentyl glycol and bisphenol A. "Bio-based", and "bio-sourced"; "biologically derived"; and "bio-derived" are used synonymously herein.

"Carbon of atmospheric origin" as used herein refers to carbon atoms from carbon dioxide molecules that have recently, in the last few decades, been free in the earth's atmosphere. Such carbons in mass are identifiable by the present of particular radioisotopes as described herein. "Green carbon", "atmospheric carbon", "environmentally friendly carbon", "life-cycle carbon", "non-fossil fuel based carbon", "non-petroleum based carbon", "carbon of atmospheric origin", and "biobased carbon" are used synonymously herein.

"Flavoring agents" are substances added to foods, beverages, cosmetics, pharmaceuticals, or medicines to improve the quality of the taste if such compositions. Oils, such as orange oils are considered flavoring agents.

Compositions in accordance with the invention include a composition comprising an ester of 1,3-propanediol and an extraction product. The esters can be a varying amount of biobased carbon depending on the compound used in the esterification. Biologically derived 1,3-propanediol contains biobased carbon. All three carbon atoms in 1,3 propanediol are biobased carbons. If the conjugate esters are formed using carboxylic acids that contain all biobased carbon, then the resulting esters also contain all biobased carbon. If, however, the carboxylic acids contain non-biobased carbons, i.e. carbons from a fossil fuel source, then the resulting ester will contain a percentage of biobased carbon in proportion to the number of carbons contributed from the carboxylic acid compared to the three carbons contributed from the biologically-derived 1,3-propanediol.

For example, distearate propanediol contains 39 carbon atoms, 18 from each of the stearic acid carbon chains and three from the 1,3-propanediol. Accordingly, if the stearic acid is non-biobased, 36 carbons out of the total 39 in distearate propanediol are non-biobased carbon. The predicted biobased content of distearate propanediol made from biologically-derived propanediol, and non-biologically derived stearic acid is 7.7 percent.

In an analysis performed using the ASTM-D6866 method, propylene glycol dibenzoate (BENZOFLEX (R) 284, Velsicol Chem. Corp. Rosemont, Ill.) was found to have 0% biobased carbon content. The same analysis of propanediol dibenzoate, synthesized using biologically-derived 1,3-propanediol had 19% bio-based carbon content. The predicted bio-based carbon content propanediol dibenzoate made from biologically-derived 1,3 propanediol is 17.6%, which is within the standard deviation of the method.

If the stearic acid in the above example is biobased, the resulting distearate propanediol would have a biobased content of 100%. Accordingly, the conjugate esters of biologically-derived 1,3-propanediol have biobased content values proportional to the biobased content of the acids used to form the esters. The esters therefore can have biobased content of at least 3% biobased carbon, at least 6% biobased carbon, at least 10% biobased carbon, at least 25% biobased carbon, at least 50% biobased carbon, at least 75% biobased carbon, and 100% biobased carbon.

The compositions comprising an extract and a conjugate ester of 1,3-propanediol can be between about 0.1% and about 5% ester, between about 0.5% and about 25% ester, between about 25% and about 50% ester, between about 50% and about 75% ester, and between about 75% and about 99% ester, and between 99% and about 100% ester.

Compositions in accordance with the invention also include compositions comprising 1,3-propanediol and an extract. The 1,3-propanediol of these compositions has at least 95% biobased carbon, or alternatively, the 1,3-propanediol has 100% biobased carbon. The compositions comprising an extract and 1,3-propanediol can be between about 0.1% and about 5% 1,3-propanediol, between about 0.5% and about 25% 1,3-propanediol, between about 25% and about 50% 1,3-propanediol, between about 50% and about 75% 1,3-propanediol, and between about 75% and about 99% 1,3-propanediol.

Compositions in accordance with the invention also include compositions comprising both 1,3-propanediol and a conjugate ester of 1,3-propanediol along with an extract. The 1,3-propanediol of these compositions has at least 95% biobased carbon, or alternatively, the 1,3-propanediol has 100% biobased carbon. The compositions comprising an extract and a mixture of 1,3-propanediol and a conjugate ester of 1,3-propanediol can be between about 0.1% and about 5% mixture, between about 0.5% and about 25% mixture, between about 25% and about 50% mixture, between about 50% and about 75% mixture, and between about 75% and about 99% mixture.

A mixture of a glycol and ester can be very effective in extractions, and the mixture can remove more active ingredients than either solvent alone. More actives are extracted from plant material using a solvent mixture because the esters (especially diesters) are non-polar, whereas glycol components are polar. Accordingly, the lipophilic ingredients can easily be removed from the plants using the ester glycol mixture. In some cases the density of an ester can be much higher than the density of the glycol, and after the maceration process the "cake" (the extract of the ester) can easily solidify and separate from the glycol phase. Additionally, the esters can be volatile compounds and in extractions the esters can be easily evaporated to obtain concrete, fragrance oil, absolute, or enfleurage.

The 1,3-propanediol, the conjugate esters of 1,3-propanediol, and mixtures thereof can be effective as solvents and diluents when combined with other appropriate solvents, including water.

Biologically-Derived 1,3-propanediol

The present invention relates to compositions comprising a botanical, vegetal, protein/peptide, marine, algae, or milk extract or fragrance concentrate or oil wherein biologically-derived 1,3-propanediol or its ester conjugate is employed as a chemical solvent for extraction or diluent of the botanical, vegetal, protein/peptide, marine, algae, or milk extract or fragrance concentrate or oil. "Biologically-derived" means that the 1,3-propanediol is synthesized by one or more species or strains of living organisms, including particularly strains of bacteria, yeast, fungus and other microbes. Biologically-derived 1,3-propanediol useful in shampoo or body wash compositions disclosed herein.

Biologically-derived 1,3-propanediol is collected in a high purity form. Such 1,3-propanediol has at least one of the following characteristics: 1) an ultraviolet absorption at 220 nm of less than about 0.200 and at 250 nm of less than about 0.075 and at 275 nm of less than about 0.075; or 2) a composition having L*a*b* "b*" color value of less than about 0.15 and an absorbance at 270 nm of less than about 0.075; or 3) a peroxide composition of less than about 10 ppm; or 4) a concentration of total organic impurities of less than about 400 ppm. A "b*" value is the spectrophotometrically determined Yellow Blue measurement as defined by the CIE L*a*b* measurement ASTM D6290.

The level of 1,3-propanediol purity can be characterized in a number of different ways. For example, measuring the remaining levels of contaminating organic impurities is one useful measure. Biologically-derived 1,3-propanediol can have a purity level of less than about 400 ppm total organic contaminants; preferably less than about 300 ppm; and most preferably less than about 150 ppm. The term ppm total organic purity refers to parts per million levels of carbon-containing compounds (other than 1,3-propanediol) as measured by gas chromatography.

Biologically-derived 1,3-propanediol can also be characterized using a number of other parameters, such as ultraviolet light absorbance at varying wavelengths. The wavelengths 220 nm, 240 nm and 270 nm have been found to be useful in determining purity levels of the composition. Biologically-derived 1,3-propanediol can have a purity level wherein the UV absorption at 220 nm is less than about 0.200 and at 240 nm is less than about 0.075 and at 270 nm is less than about 0.075.

Biologically-derived 1,3-propanediol can have a b* color value (CIE L*a*b*) of less than about 0.15.

The purity of biologically-derived 1,3-propanediol compositions can also be assessed in a meaningful way by measuring levels of peroxide. Biologically-derived 1,3-propanediol can have a concentration of peroxide of less than about 10 ppm.

It is believed that the aforementioned purity level parameters for biologically-derived and purified 1,3-propanediol (using methods similar or comparable to those disclosed in U.S. Patent Application No. 2005/0069997) distinguishes such compositions from 1,3-propanediol compositions prepared from chemically purified 1,3-propanediol derived from petroleum sources.

1,3-propanediol produced biologically via fermentation is known, including in U.S. Pat. No. 5,686,276, U.S. Pat. No. 6,358,716, and U.S. Pat. No. 6,136,576, which disclose a process using a recombinantly-engineered bacteria that is able to synthesize 1,3-propanediol during fermentation using inexpensive green carbon sources such as glucose or other sugars from plants. These patents are specifically incorporated herein by reference. Biologically-derived 1,3-propanediol can be obtained based upon use of the fermentation broth generated by a genetically-engineered $Eschericia\ coli$ ($E.\ coli$), as disclosed in U.S. Pat. No. 5,686,276. Other single organisms, or combinations of organisms, may also be used to biologically produce 1,3-propanediol, using organisms that have been genetically-engineered according to methods known in the art. "Fermentation" refers to a system that catalyzes a reaction between substrate(s) and other nutrients to product(s) through use of a biocatalyst. The biocatalysts can be a whole organism, an isolated enzyme, or any combination or component thereof that is enzymatically active. Fermentation systems useful for producing and purifying biologically-derived 1,3-propanediol are disclosed in, for example, Published U.S. Patent Application No. 2005/0069997 incorporated herein by reference.

The transformed $E.\ coli$ DH5α containing cosmid pKP1 containing a portion of the Klebsiella genome encoding the glycerol dehydratase enzyme was deposited on 18 Apr. 1995 with the ATCC under the terms of the Budapest Treaty and is identified by the ATCC number ATCC 69789. The transformed $E.\ coli$ DH5α containing cosmid pKP4 containing a portion of the Klebsiella genome encoding a diol dehydratase enzyme was deposited on 18 Apr. 1995 with the ATCC under the terms of the Budapest Treaty and is identified by the ATCC number ATCC 69790. As used herein, "ATCC" refers to the American Type Culture Collection international depository located at 10801 University Boulevard, Manassas, Va., 20110 2209, U.S.A. The "ATCC No." is the accession number to cultures on deposit with the ATCC.

The biologically derived 1,3-propanediol (bio-PDO) for use in the current invention, produced by the process described herein, contains carbon from the atmosphere incorporated by plants, which compose the feedstock for the production of bio-PDO. In this way, the bio-PDO contains only renewable carbon, and not fossil fuel based, or petroleum based carbon. Therefore the use of bio-PDO and its conjugate esters has less impact on the environment as the propanediol does not deplete diminishing fossil fuels. The use of the use of bio-PDO and its conjugate esters also does not make a net addition of carbon dioxide to the atmosphere, and thus does not contribute to greenhouse gas emissions. Thus, the present invention can be characterized as more natural and having less environmental impact than similar compositions comprising petroleum based glycols.

Moreover, as the purity of the bio-PDO utilized in the compositions of the invention is higher than chemically synthesized PDO and other glycols, risk of introducing impurities that may cause irritation is reduced by its use over commonly used glycols, such as propylene glycol.

In one embodiment of the invention, a composition comprising 1,3-propanediol and an extraction product is provided, where the 1,3-propanediol is biologically derived. The biologically-derived 1,3-propanediol can have at least 85% biobased carbon, at least 95% biobased carbon, or 100% biobased carbon, when assessed by the application of ASTM-D6866 as described above.

A sample of biologically-derived 1,3-propanediol was analyzed using ASTM method D 6866-05. The results received from Iowa State University demonstrated that the above sample was 100% bio-based content. In a separate analysis, also performed using a ASTM-D6866 method, chemical, or petroleum-based 1,3-propanediol (purchased from SHELL) was found to have 0% bio-based content. Propylene glycol (USP grade from ALDRICH) was found to have 0% bio-based content.

It is contemplated herein that other renewably-based or biologically-derived glycols, such as ethylene glycol or 1,2 propylene glycol, diethylene glycol, triethylene glycol among others, can be used in the extractions or compositions of the present invention.

There may be certain instances wherein the extractions or extract compositions of the invention may comprise a combination of a biologically-derived 1,3-propanediol and one or more non biologically-derived glycol components, such as, for example, chemically synthesized 1,3-propanediol. In such occasions, it may be difficult, if not impossible to determine which percentage of the glycol composition is biologically-derived, other than by calculating the bio-based carbon content of the glycol component. In this regard, in the extraction solvents and extract compositions of the invention, the 1,3-propanediol used as a solvent, or used to form 1,3 propanediol esters, can comprise at least about 1% bio-based carbon content up to 100% bio-based carbon content, and any percentage there between.

Ester Conjugates of Biologically Derived 1,3-Propanediol

Esters of biologically derived 1,3-propanediol, "bio-PDO" can be synthesized by contacting bio-PDO with an organic acid. The organic acid can be from any origin, preferably either a biosource or synthesized from a fossil source. Most preferably the organic acid is derived from natural sources or bio-derived having formula R₁R₂—COOH. Where in the substituent R₁ can be saturated or unsaturated, substituted or unsubstituted, aliphatic or aromatic, linear or branched hydrocarbon having chain length 1 to 40 or their salts or alkyl esters. Where in the substituent R₂ can be H or COOH. The hydrocarbon chain can also have one or more functional groups such as alkene, amide, amine, carbonyl, carboxylic acid, halide, hydroxyl groups. Naturally occurring organic acids produced esters containing all biobased carbon. These naturally occurring organic acids, especially those produced by a biological organism, are classified as bio-produced and the resulting ester or diester could thereby also be classified as bio-produced. Naturally occurring sources of such fatty acids include coconut oil, various animal tallows, lanolin, fish oil, beeswax, palm oil, peanut oil, olive oil, cottonseed oil, soybean oil, corn oil, rape seed oil. Conventional fractionation and/or hydrolysis techniques can be used if necessary to obtain the fatty acids from such materials.

Appropriate carboxylic acids for producing esters of biologically-derived 1,3-propanediol generally include: (1) C1-C3 carbon containing mono carboxylic acids, including formic acid and acetic acid; (2) fatty acids, such as those acids containing four or more carbon atoms; (3) saturated fatty acids, such as butyric acid, caproic acid, valeric acid, caprylic acid, capric acid, lauric acid, myristic acid, palmitic acid, stearic acid, arachidic acid, and behenic acid; (4) unsaturated fatty acids, such as oleic acid, linoleic acid, and euricic acid; (5) polyunsaturated fatty acids, such as alpha-linolenic acid, stearidonic acid (or moroctic acid), eicosatetraenoic acid, omega-6 fatty acids, arachidonic acids, and omega-3 fatty acids, eicosapentaenoic acid (or timnodonic acid), dosocapentaenoic acid (or clupanodonic acid), and docosahexaenoic acid (or cervonic acid); (6) hydroxy fatty acids, such as 2-hydroxy linoleic acid, and recinoleic acid; phenylalkanoic fatty acids, such as 11-phenyl undecanoic acid, 13-phenyl tridecanoid acid, and 15-phenyl tridecanoid acid; and (7) cyclohexyl fatty acids, such as 11-cyclohexyl undecanoic acid, and 13-cyclohexyl tridecanoic acid.

The following acids and their salts or alkyl esters are specifically useful, acetic, butyric, lauric, myristic, palmitic, stearic, arachidic, adipic, benzoic, caprylic, maleic, palmitic, sebacic, archidonic, erucic, palmitoleic, pentadecanoic, heptadecanoic, nondecanoic, octadectetraenoic, eicosatetraenoic, eicosapentaenoic, docasapentaenoic, tetracosapentaenoic, tetrahexaenoic, docosahexenoic, (alpha)-linolenic, docosahexaenoic, eicosapentaenoic, linoleic, arachidonic, oleic, erucic, formic, propionic, valeric, caproic, capric, malonic, succinic, glutaric, adipic, pimelic, suberic, azelaic, tartaric, citric, salicylic, acetyl-salicylic, pelargonic, behenic, cerotic, margaric, montanic, melissic, lacceroic, ceromelissic, geddic, ceroplastic undecylenic, ricinoleic, and elaeostearic acid as well as mixtures of such acids. A more preferred list of suitable organic acids are acetic, adipic, benzoic, maleic, sebacic, and mixtures of such acids. A more preferred list of suitable "fatty acids" meaning generally acids named containing 8-40 carbon in the carbon useful in the present invention include butyric, valeric, caproic, caprylic, pelargonic, capric, lauric, myristic, palmitic, stearic, arachidic, behenic, cerotic, oleic, linoleic, linolenic, margaric, montanic, melissic, lacceroic, ceromelissic, geddic, ceroplastic and the mixtures of such acids. Among those acids, these acids, and their salts and alkyl esters are most preferred stearic, lauric, palmetic, oleic, 2-ethyl hexanoic, and 12-hydroxystearic and mixtures of such acids.

The esters produced include all the appropriate conjugate mono and diesters of 1,3 propanediol using the described organic acids. Some esters in particular that are produced include propanediol distearate and monostearate, propandiol dilaurate and monolaurate, propanediol dioleate and monooleate, propanediol divalerate and monovalerate, propanediol dicaprylate and monocaprylate, propanediol dimyristate and monomyristate, propanediol dipalmitate and monopalmitate, propanediol dibehenate and monobehenate, propanediol adipate, propanediol maleate, propanediol dibenzoate, propanediol diacetate, and all mixtures thereof.

In particular, the esters produced include: propanediol distearate and monostearate, propanediol dioleate and monooleate, propanediol dicaprylate and monocaprylate, propanediol dimyristate and monomyristate, and all mixtures thereof.

Generally 1,3-propanediol can be contacted, preferably in the presence of an inert gas reacted with a fatty acid or mixture of fatty acids or salts of fatty acids in the absence or presence of a catalyst or mixture of two or more catalysts, at temperatures ranging from 25° C. to 400° C.

During the contacting, water is formed and can be removed in the inert gas stream or under vacuum to drive the reaction complete. Any volatile byproducts can be removed similarly. When the reaction is complete, the heating can be stopped and cooled.

The catalyst can be removed preferably by dissolving and removing in deionized water. If catalyst can be removed by treating with deionized water, the reaction mixture is treated with aqueous solutions of acid or base to forms salts and removing the salts either by washing or filtering.

Further purification to obtain high purity fatty esters, preferably for pharmaceutical application can be carried out by dissolving in a solvent that dissolves fatty ester easily at higher temperatures and least at lower temperatures and recrystallizing with or without addition of additional solvent at low temperatures.

The catalyst can be an acid for non-limiting examples, sulfuric acid, or p-toluene sulfonic acid. The catalyst can also be a base, for non-limiting example, sodium hydroxide. The catalyst can also be a salt, for non-limiting example, potassium acetate. The catalyst can also be an alkoxide, for non-limiting example, titanium tetraisopropoxide. The catalyst can also be a heterogeneous catalyst, for non-limiting examples: zeolite, heteropolyacid, amberlyst, or ion exchange resin. The catalyst can also be a metal salt, for non-limiting examples, tin chloride, or copper chloride, The catalyst can also be an enzyme, such as those known in the art. The catalyst can also be an organic acid, for a non-limiting example, formic acid. Finally the catalyst can also be an organometallic compound, for non-limiting example, n-butylstannoic acid.

This process can be carried out in the presence or absence of a solvent. If a solvent is not necessary to facilitate the production of fatty ester, it is preferred that the process is carried out in the absence of solvent.

The process can be carried out at atmospheric pressure or under vacuum or under pressurized conditions.

Reaction 1 (diester)

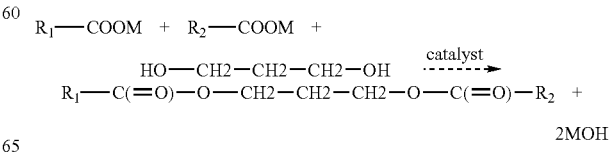

+ 2MOH

Where $R_1$ and $R_2$ is a hydrocarbon, preferably with a carbon chain length of about 1 to about 40. Such hydrocarbons can be saturated or unsaturated, substituted or unsubstituted, linear or branched M is hydrogen, an alkali metal or an alkyl group.

Reaction 2 (monoester)

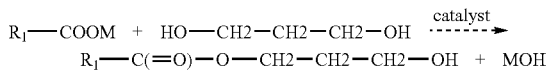
$$R_1-C(=O)-O-CH_2-CH_2-CH_2-OH + MOH$$

Where $R_1$ is a hydrocarbon, preferably with a carbon chain length of about 1 to about 40. Such hydrocarbons can be saturated or unsaturated, substituted or unsubstituted, linear or branched. M is hydrogen, an alkali metal or an alkyl group.

Compositions in accordance with the invention comprise esters in which R1 has one or more functional groups selected from the group consisting of alkene, amide, amine, carbonyl, carboxylic acid, halide, hydroxyl groups, ether, alkyl ether, sulfate and ethersulfate. The esters can have the formula R1-C(=O)-O-CH2-CH2-CH2-O-C(=O)-R2, wherein both R1 and R2 are linear or branched carbon chains of a length between about 1 an about 40 carbons. R1 and R2 can have one or more functional groups selected from the group consisting of alkene, amide, amine, carbonyl, carboxylic acid, halide, hydroxyl groups, ether, alkyl ether, sulfate and ethersulfate. Additionally, R1 and R2 can be the same carbon chain in the case of a diester.

Any molar ratio of diol to dicarboxylic acid or its salt or its ester can be used. The preferred range of the diol to dicarboxylic acid is from about 1:3 to about 2:1. This ratio can be adjusted to shift the favor of the reaction from monoester production to diester production. Generally, to favor the production of diesters slightly more than about a 1:2 ratio is used; whereas to favor the production of monoesters about a 1:1 ratio is used. In general, if the diester product is desired over the monoester the ratio of diol to dicarboxylic acid can range from about 1.01:2 to about 1.1:2; however if the monoester is desired a range of ratios from about 1.01:1 to about 2:1 is used.

The catalyst content for the reaction can be from 1 ppm to 60 wt % of the reaction mixture, preferably from 10 ppm to 10 wt %, more preferably from 50 ppm to 2 wt % of the reaction mixture.

The product may contain diesters, monoesters or combination diesters and monoesters and small percentage of unreacted acid and diol depending on the reaction conditions. Unreacted diol can be removed by washing with deionized water. Unreacted acid can be removed by washing with deionized water or aqueous solutions having base or during recrystallization.

Any ester of 1,3-propanediol can be made or used in accordance with the present invention. Short, middle and long chain monoesters and diesters of the 1,3-propanediol can be made. Specifically those acids containing between about 1 and about 36 carbons in the alkyl chain can be produced. More specifically, the following monoesters and diesters can be produced: propanediol distearate (monostearate and the mixture), propandiol dilaurate (monolaurate and the mixture), propanediol dioleate (monooleate and the mixture), propanediol divalerate (monovalerate and the mixture), propanediol dicaprylate (monocaprylate and the mixture), propanediol dimyristate (monomyristate and the mixture), propanediol dipalmitate (monopalmitate and the mixture), propanediol dibehenate (monobehenate and the mixture), propanediol adipate, propanediol maleate, propanediol dibenzoate, and propanediol diacetate.

For compositions comprising an extract and 1,3-propanediol, the conjugate esters of 1,3-propanediol, or mixtures thereof, the extract can be a compound or group of compounds that are extracted from a source material. In some applications, the extract is extracted from a natural source, such as a botanical source. Examples of appropriate natural extracts include botanical extracts, vegetal extracts, protein extracts, lipid extracts, marine extracts, algae extracts, and milk extracts.

Botanical sources for extracts include the following list of families of plants and trees: Acanthaceae, Aceraceae, Achariaceae, Achatocarpaceae, Acoraceae, Actinidiaceae, Actiniopteridaceae, Adiantaceae, Adoxaceae, Aegicerataceae, Aetoxicaceae, Agavaceae, Agdestidaceae, Aitoniaceae, Aizoaceae, Akaniaceae, Alangiaceae, Alismataceae, Alliaceae, Alseuosmiaceae, Alstroemeriaceae, Altingiaceae, Alzateaceae, Amaranthaceae, Amaryllidaceae, Amborellaceae, Ampelidaceae, Anacardiaceae, Anarthriaceae, Ancistrocladaceae, Androstachydaceae, Anemiaceae, Angiopteridaceae, Anisophylleaceae, Annonaceae, Anthericaceae, Antoniaceae, Aphyllanthaceae, Apiaceae, Apocynaceae, Aponogetonaceae, Apostasiaceae, Aquifoliaceae, Araceae, Araliaceae, Araucariaceae, Arecaceae, Aristolochiaceae, Asclepiadaceae, Asparagaceae, Asphodelaceae, Aspidiaceae, Aspleniaceae, Asteliaceae, Asteraceae, Asteranthaceae, Asteranthaceae, Asteranthaceae, Asteranthaceae, Aucubaceae, Austrobaileyaceae, Avicenniaceae, Azollaceae, Balanopaceae, Balanophoraceae, Balsaminaceae, Bambuseae, Barringtoniaceae, Basellaceae, Bataceae, Begoniaceae, Berberidaceae, Betulaceae, Bignoniaceae, Bischofiaceae, Bixaceae, Blechnaceae, Bombacaceae, Bonnetiaceae, Boraginaceae, Botrychiaceae, Brassicaceae, Bruniaceae, Brunoniaceae, Buddlejaceae, Burmanniaceae, Burseraceae, Butomaceae, Buxaceae, Byblidaceae, Byttneriaceae, Cabombaceae, Cactaceae, Caesalpiniaceae, Callitrichaceae, Calycanthaceae, Calyceraceae, Campanulaceae, Canellaceae, Cannabidaceae, Cannaceae, Canotiaceae, Capparidaceae, Caprifoliaceae, Cardiopteridaceae, Caricaceae, Carlemanniaceae, Caryocaraceae, Caryophyllaceae, Casuarinaceae, Cayceraceae, Cecropiaceae, Celastraceae, Centrolepidaceae, Cephalotaceae, Cephalotaxaceae, Ceratophyllaceae, Cercidiphyllaceae, Cheiropleuriaceae, Chenopodiaceae, Chloanthaceae, Chloranthaceae, Christenseniaceae, Chrysobalanaceae, Cistaceae, Clethraceae, Clusiaceae, Cneoraceae, Cochlospermaceae, Columelliaceae, Combretaceae, Commelinaceae, Compositae, Connaraceae, Conocephalaceae, Convolvulaceae, Coriariaceae, Cornaceae, Corynocarpaceae, Costaceae, Crassulaceae, Crossosomataceae, Crypteroniaceae, Cryptogram maceae, Cucurbitaceae, Culcitaceae, Cunoniaceae, Cupressaceae, Cyanastraceae, Cyatheaceae, Cycadaceae, Cyclanthaceae, Cyclocheilaceae, Cymodoceaceae, Cynomoriaceae, Cyperaceae, Cypripediaceae, Cyrillaceae, Danaeaceae, Daphniphyllaceae, Datiscaceae, Davalliaceae, Davidsoniaceae, Degeneriaceae, Dennstaedtiaceae, Dialypetalanthaceae, Diapensiaceae, Dichapetalaceae, Dicksoniaceae, Dicrastylidaceae, Didiereaceae, Didymelaceae, Diegodendraceae, Dilleniaceae, Dioscoreaceae, Dipsacaceae, Dipteridaceae, Dipterocarpaceae, Dracaenaceae, Droseraceae, Dryopteridaceae, Dysphaniaceae, Dysphaniaceae, Ebenaceae, Ecdeiocoleaceae, Elaeagnaceae, Elaeocarpaceae, Elaphoglossaceae, Elatinaceae, Empetraceae, Epacridaceae, Ephedraceae, Equisetaceae, Ericaceae, Eriocaulaceae, Erythropalaceae, Erythroxylaceae, Escalloniaceae, Eucommiaceae, Eucryphiaceae, Euphorbiaceae, Eupomatiaceae, Eupteleaceae, Fabaceae, Fagaceae, Flacourtiaceae, Flagellariaceae, Fouquieriaceae, Frankeniaceae, Fumariaceae, Garryaceae, Geissolomataceae, Gentianaceae, Geosiridaceae, Geraniaceae, Gesneriaceae, Ginkgoaceae, Gleicheniaceae, Globulariaceae, Gnetaceae, Goetzeaceae, Gomortegaceae, Goodeniaceae, Goupiaceae, Gramineae, Grammitaceae, Grammitidaceae, Grubbiaceae, Gunneraceae, Guttiferae, Gyrostemonaceae, Haemodoraceae, Haloragaceae, Haloragidaceae, Hamamelidaceae, Heliconiaceae, Helminthostachyaceae, Hemionitidaceae, Hernandiaceae, Heteropyxidaceae, Himantandraceae, Hippocastanaceae, Hippocrateaceae, Hippuridaceae, Hoplestigmataceae, Hostaceae, Humiriaceae, Hydnoraceae, Hydrangeaceae, Hydrocharitaceae, Hydrocotylaceae, Hydrophyllaceae, Hydrostachyaceae, Hymenophyllaceae, Hymenophyllopsidaceae, Hypericaceae, Hypolepidaceae, Hypoxidaceae, Icacinaceae, Idiospermaceae, Illiciaceae, Iridaceae, Isoetaceae, Ixonanthaceae, Juglandaceae, Julianiaceae, Juncaceae, luncaginaceae, Koeberliniaceae, Krameriaceae, Labiatae, Lacistemataceae, Lactoridaceae, Lamiaceae, Lardizabalaceae, Lauraceae, Lecythidaceae, Leeaceae, Leguminosae, Leitneriaceae, Lemnaceae, Lennoaceae, Lentibulariaceae, Lilaeaceae, Liliaceae, Limnanthaceae, Limnocharitaceae, Linaceae, Lindsaeaceae, Lissocarpaceae, Loasaceae, Lobeliaceae, Loganiaceae, Lomariopsidaceae, Lophosoriaceae, Loranthaceae, Lowiaceae, Loxogrammaceae, Loxsomaceae, Lunulariaceae, Luzuriagaceae, Lycopodiaceae, Lygodiaceae, Lythraceae, Magnoliaceae, Malesherbiaceae, Malpighiaceae, Malvaceae, Marantaceae, Marattiaceae, Marcgraviaceae, Marchantiaceae, Marsileaceae, Martyniaceae, Matoniaceae, Mayacaceae, Medusagynaceae, Medusandraceae, Melastomataceae, Meliaceae, Melianthaceae, Menispermaceae, Menyanthaceae, Metaxyaceae, Mimosaceae, Misodendraceae, Monimiaceae, Moraceae, Moraceae, Moringaceae, Musaceae, Myoporaceae, Myricaceae, Myristicaceae, Myrothamnaceae, Myrsinaceae, Myrtaceae, Najadaceae, Negripteridaceae, Nelumbonaceae, Nepenthaceae, Nephrolepidaceae, Nolanaceae, Nyctaginaceae, Nymphaeaceae, Nyssaceae, Ochnaceae, Octoknemaceae, Olacaceae, Oleaceae, Oleandraceae, Oliniaceae, Onagraceae, Oncothecaceae, Onocleaceae, Ophioglossaceae, Opiliaceae, Orchidaceae, Orobanchaceae, Osmundaceae, Oxalidaceae, Paeoniaceae, Pandaceae, Pandanaceae, Papaveraceae, Parkeriaceae, Passifloraceae, Pedaliaceae, Penaeaceae, Pentaphragmataceae, Pentaphylaceae, Peperomiaceae, Peraceae, Peranemaceae, Periplocaceae, Petrosaviaceae, Philesiaceae, Philydraceae, Phormiaceae, Phrymaceae, Phytolaccaceae, Pinaceae, Piperaceae, Pittosporaceae, Plagiogyriaceae, Plantaginaceae, Platanaceae, Platyzomataceae, Plumbaginaceae, Poaceae, Podocarpaceae, Podophyllaceae, Podostemaceae, Polemoniaceae, Polygalaceae, Polygonaceae, Polypodiaceae, Pontederiaceae, Portulacaceae, Potaliaceae, Potamogetonaceae, Primulaceae, Proteaceae, Psilotaceae, Pteridaceae, Punicaceae, Pyrolaceae, Quiinaceae, Rafflesiaceae, Ranunculaceae, Rapateaceae, Rebouliaceae, Resedaceae, Restionaceae, Rhamnaceae, Rhizophoraceae, Rhoipteleaceae, Rhoipteleaceae, Rhopalocarpaceae, Roridulaceae, Rosaceae, Rubiaceae, Ruscaceae, Rutaceae, Sabiaceae, Saccifoliaceae, Salicaceae, Salvadoraceae, Salviniaceae, Santalaceae, Sapindaceae, Sapotaceae, Sarcolaenaceae, Sarcospermataceae, Sarraceniaceae, Saururaceae, Saxifragaceae, Scheuchzeriaceae, Schisandraceae, Schizaeaceae, Scrophulariaceae, Scyphostegiaceae, Scytopetalaceae, Selaginaceae, Selaginellaceae, Simaroubaceae, Sinopteridaceae, Smilacaceae, Solanaceae, Sonneratiaceae, Sparganiaceae, Sphaerosepalaceae, Sphenostemonaceae, Stachyuraceae, Stackhousiaceae, Staphyleaceae, Stemonaceae, Sterculiaceae, Strasburgeriaceae, Strelitziaceae, Stromatopteridaceae, Strychnaceae, Styracaceae, Symplocaceae, Taccaceae, Taenitidaceae, Tamaricaceae, Taxaceae, Taxodiaceae, Tecophilaeaceae, Tepuianthaceae, Tetracentraceae, Tetragoniaceae, Tetrameristaceae, Theaceae, Theligonaceae, Thelypteridaceae, Theophrastaceae, Thunbergiaceae, Thurniaceae, Thymelaeaceae, Thyrsopteridaceae, Tichodendraceae, Tiliaceae, Tmesipteridaceae, Tovariaceae, Trapaceae, Tremandraceae, Trigoniaceae, Trilliaceae, Triuridaceae, Trochodendraceae, Tropaeolaceae, Turneraceae, Typhaceae, Uapacaceae, Ulmaceae, Urticaceae, Vacciniaceae, Vahliaceae, Valerianaceae, Velloziaceae, Verbenaceae, Violaceae, Vitaceae, Vittariaceae, Vivianiaceae, Vochysiaceae, Welwitschiaceae, Winteraceae, Xanthorrhoeaceae, Xyridaceae, Zamiaceae, Zingiberaceae, Zosteraceae, Zygophyllaceae.

Preferred families of plants and trees include Anacardiaceae Araceae, Balanopaceae, Balsaminaceae, Begoniaceae, Boraginaceae, Buxaceae, Caricaceae, Cucurbitaceae, Clusiaceae, Daphniphyllaceae, Ericaceae, Euphorbiaceae, Fabaceae, Fagaceae, Hippocastanaceae, Hostaceae, Hydrangeaceae, Labiateae, Lilaeaceae, Magnoliaceae, Moringaceae, Myristicaceae, Myrtaceae, Oleaceae, Orchidaceae, Peperomiaceae, Pinaceae, Primulaceae, and Rutaceae.

The preferred species of plants and trees for extract sources include *Achillea millefolium, Aesculus chinensis, Allium sativum, Artemisia apiacea, Astrocaryum murumuru, Bactris gasipaes, Benincasa hispida, Celastrus paniculatus, Cetraria islandica, Chenopodium quinoa, Cinchona succirubra, Citrus bergamia, Citrus sinensis, Coriandrum sativum, Codium tomentosum, Commiphora molmol, Crataegus cuneata, Cucumis sativus, Eucalyptus globulus, Gleditsia sinensis, Gnetum amazonicum, Hibiscus rosa-sinensis, Jasminum officinale, Lonicera caprifolium, Lonicera japonica, Lycopersicon esculentum, Malus pumila, Matricaria recutita, Maximiliana maripa, Melaleuca hypericifolia, Melaphis chinensis, Mentha piperita, Mouriri apiranga, Nasturtium officinale, Nelumbo nucifera, Oenothera biennis, Ophiopogon japonicus, Persea americana, Paffia paniculata, Phellodendron amurense, Phyllanthus emblica, Pisum sativum, Potentilla erecta, Pterocarpus santalinus, Rehmannia chinensis, Reseda luteola, Ribes nigrum, Rosa centifolia, Rubus thunbergii, Spondias amara, Styrax benzoin,* and *Thymus vulgaris.*

Extract sources also include algae. Families of algae used as extract sources include Acrochaeticaceae, Characeae, Codiaceae, Fucaceae, Laminariaceae, Lemaneaceae, Ulvaceae, and Pamariaceae. Preferred algae species include *Lemanea fluviatilis* (red algea), (L.), *Ascophyllum nodosum* (brown alga), *Lemanea fluviatilis, Lemanea fucina* (red algea), *Ulva lactuca* (green alga), *Laminaria digitata, Laminaria ochroleuca.*

Extract sources also include members of the kingdom of Fungi. For extraction, classes of Homobasidiomycetes (or true mushrooms) can be used. Some exemplary mushrooms families include: Meripilaceae, Tricholomataceae, and Ganodermataceae (maitake, shiitake, reishi mushrooms). Specific species include: *Agaricus bisporus, Agaricus campestris, Flammulina velutipes Hypsizygus tessulatus, Lentinus edodes, Phellinus linteus, Pleurotus cornucopiae, Pleurotus ostreatus, Tremella fuciformis, Sparassis crispa, Tuber magnatum,* and *Volvariella volvacea.*

Species from the division of Bryophyta, Kingdom of plantae (which includes mosses) can be used as extract sources, and some species of lichen can also be used for extraction.

Marine sources, such as plants, algae, plankton, and fish, are used to produce extracts. Protein and lipid extract sources include plant, animal, fish and human (e.g. Placenta) materials. Milk can be used as an extract source to isolate and concentrate proteins, peptides, and lipids.

All of the compositions and methods disclosed and claimed herein can be made and executed without undue experimentation in light of the present disclosure. While the compositions and methods of the present disclosure have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are chemically related may be substituted for the agents described herein while the same or similar results would be achieved. All such similar substitutes and modifications apparent to those skilled in the art are deemed to be within the spirit, scope, and concept of the invention as defined by the appended claims.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

All ingredients used in the preparation of the personal care compositions described in the following Examples are available commercially unless otherwise noted.

The meaning of abbreviations used is as follows "% wt." means percent by weight; "qs" means as much as suffices; "EDTA" means ethylenediamine tetraacetate; "° C." means degrees Centigrade; "° F." is degrees Fahrenheit, "Bio-PDO" means biologically-derived 1,3-propanediol; "ppm" is parts per million; "AU" is absorbance unit; "nm" is nanometer(s); "GC" is gas chromatograph; "APHA" is American Public Health Association; "cps" is centipoise; "f/t" is freeze/thaw; "mPa·s" is milliPascal seconds; "D.I." is deionized.

General Methods:

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass. 1989.

All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Glycerol used in the production of 1,3-propanediol was obtained from J. T. Baker Glycerin USP grade, Lot 325608 and G19657.

Differential Scanning Calorimetry: DSC thermograms were recorded using Universal V3 1A TA instrument under constant stream of nitrogen with a heating and cooling rate of 10° C./min.

NMR: 1H NMR spectra were recorded on Bruker DRX 500 using XWINNMR version 3.5 software. Data was acquired using a 90 degree pulse (p1) and a 30 second recycle delay (d1). Samples were dissolved in deuterated chloroform and nondeuterated chloroform was used as internal standard.

Isolation and Identification Bio-PDO

The conversion of glycerol to bio-PDO was monitored by HPLC. Analyses were performed using standard techniques and materials available to one of skill in the art of chromatography. One suitable method utilized a Waters Maxima 820 HPLC system using UV (210 nm) and RI detection. Samples were injected onto a Shodex SH-1011 column (8 mm×300 mm, purchased from Waters, Milford, Mass.) equipped with a Shodex SH-1011P precolumn (6 mm×50 mm), temperature controlled at 50° C., using 0.01 N H2SO4 as mobile phase at a flow rate of 0.5 mL/min. When quantitative analysis was desired, samples were prepared with a known amount of trimethylacetic acid as external standard. Typically, the retention times of glycerol (RI detection), 1,3-propanediol (RI detection), and trimethylacetic acid (UV and RI detection) were 20.67 min, 26.08 min, and 35.03 min, respectively.

Production of bio-PDO was confirmed by GC/MS. Analyses were performed using standard techniques and materials available to one of skill in the art of GC/MS. One suitable method utilized a Hewlett Packard 5890 Series II gas chromatograph coupled to a Hewlett Packard 5971 Series mass selective detector (EI) and a HP-INNOWax column (30 m length, 0.25 mm i.d., 0.25 micron film thickness). The retention time and mass spectrum of 1,3-propanediol generated from glycerol were compared to that of authentic 1,3-propanediol (m/e: 57, 58).

Production of Bio-Based Monoesters and Diesters from Bio-Produced 1,3-propanediol.

Monoesters and diester of bio-produced 1,3-propandiol may be produced by combining bioPDO with organic acid. The combination is to be preformed in dry conditions under heat and prolong agitation with a selected catalyst. The ratio of monoester to diester produced will vary according to the molar ratio of acid to bioPDO and the selection of catalyst.

The production of esters was confirmed using $^1$H nuclear magnetic resonance. Analyses were performed using standard techniques and materials available to one of skill in the art of $^1$H NMR.

Proton Nuclear Magnetic Resonance ($^1$H NMR) Spectroscopy is a powerful method used in the determination of the structure of unknown organic compounds. It provides information concerning: the number of different types of hydrogens present in the molecule, the electronic environment of the different types of hydrogens and the number of hydrogen "neighbor" a hydrogen has.

The hydrogens bound to carbons attached to electron withdrawing groups tend to resonate at higher frequencies from TMS, tetramethylsilane, a common NMR standard. The position of where a particular hydrogen atom resonates relative to TMS is called its chemical shift (δ). Typical chemicals shifts of fatty ester are as follows.

δ=0.88 for terminal $CH_3$

δ=1.26, 1.61 and 1.97 for methylene groups of (—$CH_2$—C$\underline{H}_2$—$CH_2$), (C$\underline{H}_2$—$CH_2$—C=O) and (O—$CH_2$—C$\underline{H}_2$—$CH_2$—O) respectively, δ=2.28 for methylene group adjustcent to ester (C$\underline{H}_2$—C=O)

δ=4.15 for ester (C(=O)—O—C$\underline{H}_2$—).

Proton NMR can distinguish the protons corresponding to the end groups (C$\underline{H}_2$—OH) (δ=3.7) from that of the middle ester groups (C$\underline{H}_2$—O—C(=O)—) (δ=4.15 and 4.24 for diester and monoester, respectively) and thus it is possible to identify ester and can monitor the reaction by comparing the integral areas of these two peaks.

$$\% \text{ Esterification} = \frac{\text{Combined areas of peaks at 41.5 and 4.24} \times 100}{\text{Combined areas of peaks at 3.70, 41.5 and 4.24}}$$

Example 1

Conversion of D-glucose to 1,3-Propanediol Under Fermentation Conditions

E. coli strain ECL707, containing the K. pneumoniae dha regulon cosmids pKP1 or pKP2, the K. pneumoniae pdu operon pKP4, or the Supercos vector alone, is grown in a 5 L Applikon fermenter for the production of 1,3-propanediol from glucose.

The medium used contains 50-100 mM potassium phosphate buffer, pH 7.5, 40 mM (NH4)2SO4, 0.1% (w/v) yeast extract, 10 μM CoCl2, 6.5 μM CuCl2, 100 μM FeCl3, 18 μM FeSO4, 5 μM H3BO3, 50 μM MnCl2, 0.1 μM Na2MoO4, 25 μM ZnCl2, 0.82 mM MgSO4, 0.9 mM CaCl2, and 10-20 g/L glucose. Additional glucose is fed, with residual glucose maintained in excess. Temperature is controlled at 37° C. and pH controlled at 7.5 with 5N KOH or NaOH. Appropriate antibiotics are included for plasmid maintenance. For anaerobic fermentations, 0.1 vvm nitrogen is sparged through the reactor; when the dO setpoint was 5%, 1 vvm air is sparged through the reactor and the medium is supplemented with vitamin B12.

Titers of 1,3-propanediol (g/L) range from 8.1 to 10.9. Yields of bio-PDO (g/g) range from 4% to 17%.

Example 2

Purification of Biosourced 1,3-Propanediol

Published U.S. Patent Application No. 2005/0069997 discloses a process for purifying 1,3-propanediol from the fermentation broth of a cultured E. coli that has been bioengineered to synthesize 1,3-propanediol from sugar. The basic process entails filtration, ion exchange and distillation of the fermentation broth product stream, preferably including chemical reduction of the product during the distillation procedure.

1,3-Propanediol, produced as recited in Example 1, was purified, by a multistep process including broth clarification, rotary evaporant, anion exchange and multiple distillation of the supernatant.

At the end of the fermentation, the broth was clarified using a combination of centrifugation and membrane filtration for cell separation, followed by ultrafiltration through a 1000 MW membrane. The clarified broth processed in a large rotary evaporator. Approximately 46 pounds of feed material (21,000 grams) were processed to a concentrated syrup. A 60 ml portion of syrup was placed in the still pot of a 1" diameter distillation column. Distillation was conducted at a vacuum of 25 inches of mercury. A reflux ratio of approximately 1 was used throughout the distillation. Several distillate cuts were taken, the central of which received further processing. The material was diluted with an equal volume of water, the material was loaded onto an anion exchange column (mixed bed, 80 grams of NM-60 resin), which had been water-washed. Water was pumped at a rate of 2 ml/min, with fractions being collected every 9 minutes. Odd number fractions were analyzed, and fractions 3 through 9 contained 3 G. The fractions containing 3 G were collected and subjected to microdistillation to recover several grams of pure 1,3-propanediol monomer (which was polymerized to mono and diesters according the methods described in Example 2-8).

Example 3

Production of Propanediol Distearate Using P-toluenesulfonic Acid as Catalyst To prepare propanediol distearate from biosource 1,3-propanediol and stearic acid, biosource 1,3-propanediol was purified using methods as in examples 1 and 2. 2.58 g (0.033 moles) of biosource 1,3-propanediol, 19.45 g (0.065 moles) of stearic acid (Aldrich, 95%), and 0.2125 g (0.001 moles) of p-toluenesulfonic acid (Aldrich 98.5%) were charged into glass reactor fitted with mechanical stirrer and the reactor was flushed with dry nitrogen gas to remove air and moisture for 15 min. Then reaction temperature was raised to 100° C. while thoroughly stirring the reaction mixture under nitrogen flow and continued for 210 min.

After completion of the reaction, reaction mixture was cooled to about 35° C. and the product was transferred into a beaker. The product was purified by adding 100 mL of water and thoroughly stirring at 45-60° C., to form an emulsion for 15 min. The mixture was cooled and the solid propanediol distearate was separated by filtration.

The product was characterized by $^1$H NMR (Nuclear Magnetic Resonance) spectra ($CDCl_3$ (deuterated chloroform)): δ=0.88 (t, C$\underline{H}_3$—$CH_2$, 6H), 1.26 (t, $CH_2$—C$\underline{H}_2$—$CH_2$, 28H), 1.61 (t, C$\underline{H}_2$—$CH_2$—C=O, 4H), 1.97 (t, —O—$CH_2$—C$\underline{H}_2$—$CH_2$—O, 2H), 2.28 (t, C$\underline{H}_2$—C=O, 4H), 4.15 (t, C(=O)—O—C$\underline{H}_2$-4H) and DSC (Tm=66.4° C. and Tc=54.7° C.).

Example 4

Purity Characterizations of Biologically-Derived 1,3-Propanediol

In Table 1 below, biologically-derived 1,3-propanediol (produced and purified as described in Published U.S. Patent Application No. 2005/0069997) ("Bio-PDO") is compared, in several purity aspects, to two separate commercially-obtained preparations of chemically-produced 1,3-propanediol (Source A and B).

TABLE 1

|  | Units | Source A | Source B | Bio-PDO |
|---|---|---|---|---|
| Total Org Impurities | ppm | 570 | 695 | 80 |
| UV Abs 220 nm, | AU | 0.25 | 1.15 | 0.12 |
| UV Abs 250 nm, | AU | 0.123 | 0.427 | 0.017 |

TABLE 1-continued

| | Units | Source A | Source B | Bio-PDO |
|---|---|---|---|---|
| UV Abs 275 nm | AU | 0.068 | 0.151 | 0.036 |
| UV Abs 350 nm | AU | 0.013 | 0.007 | 0.001 |
| Peroxides | ppm | 67 | 43 | 2 |
| CIE L*a*b* ASTM D6290 | b* | 0.411 | 0.03 | 0.1 |
| Carbonyls | ppm | 147 | 175 | 1 |

A typical profile of purity aspects are provided in Table 2 below, on a sample of biologically-produced 1,3-propanediol purified by a process disclosed in Published U.S. Patent Application No. 2005/0069997.

TABLE 2

| | | Units |
|---|---|---|
| 1,3-Propanediol | GC area % | 99.992 |
| pH, neat | pH | 8.22 |
| UV Abs. @ 270 nm, 1:5 dilution | AU | 0.01 |
| Color APHA | | 3 |
| Color (Process Measurement) L*a*b* | b* | 0.10 |
| Water | ppm | 115 |
| UV abs 220 nm neat | AU | 0.144 |
| UV abs 250 nm neat | AU | 0.017 |
| UV abs 275 nm neat | AU | 0.036 |
| UV abs 350 nm neat | AU | 0.001 |
| Peroxide | ppm | 2 |
| Metals | ppm | <1 |
| Sulfur | ppm | <1 |
| Carbonyl | ppm | 1 |

The unit ppm of total organic impurities means parts per million of total organic compounds in the final preparation, other than 1,3-propanediol, as measured by a gas chromatograph with a flame ionization detector. Results are reported by peak area. A flame ionization detector is insensitive to water, so the total impurity is the sum of all non 1,3-propanediol organic peaks (area %) ratioed to the sum of all area % (1,3-propanediol included). The term "organic materials" refers to the contaminants containing carbon.

The tables show that the disclosed method of purification provides for highly pure biologically derived 1,3-propanediol, as compared to commercially-obtained preparations of chemically-produced 1,3-propanediol.

Example 5

Skin Irritation and Sensitization Characterization of Biologically-Derived 1,3-Propanediol In a human skin patch test with approximately 100 subjects, 5, 25, and 50% PDO did not cause any skin reactions indicative of irritation or sensitization. A second human skin patch test did not produce any clinically significant dermal irritation or sensitization reactions with concentrations of 25, 50, and 75% PDO at pH 7, or 75% PDO at pH 4 and 9. Based on these studies PDO is not expected to be a skin irritant or sensitizer in humans. In the second human skin patch test, propylene glycol (1,2-propanediol or PG) was also tested at 25, 50, and 75% (pH 7) and all three concentrations of PG were patch test irritants and cumulative irritants for human skin.

Examples 6-8 are prophetic and are based on a descriptions from: D'Amelio, Frank S Sr.; *Botanicals: A Phytocosmetic Desk Reference*; CRC Press 1999, pg. 299-304.

Example 6

| A Natural, High Foaming, Gentle Shampoo for Everyday Use | | | |
|---|---|---|---|
| Percent | Sequence | Raw Material | INCI Name |
| 1.00 | 1 | Deionized Water | Water |
| 0.00 | 1 | Saponins | Saponins |
| 0.00 | 1 | Cocamidopropyl Betaine | Cocamidopropyl Betaine |
| .00 | 1 | Cocamide DEA 1:1 | Cocamide DEA |
| .10 | 1 | Horsetail Extract, 5:1 BIO-PDO | Horsetail Extract |
| .10 | 1 | Comfrey Leaf Extract, 5:1 BIO-PDO | Comfrey Leaf Extract |
| .10 | 1 | Rosemary Extract, 5:1 BIO-PDO | Rosemary Extract |
| .10 | 1 | Chamomile Extract, 5:1 BIO-PDO | Matricaria Extract |
| .s. | 2 | 50% Aq. Sodium Hydroxide | Sodium Hydroxide |
| .50 | 3 | Aculyn 22 Thickener[1] | Acrylates/Steareth-20 Methacrylate Copolymer |
| 5.00 | 4 | Plantaren 2000[2] | Decyl Polyglucose |
| .10 | | Lipovol A[3] | Avacado Oil |
| .s. | 5 | 25% Aqueous Citric Acid | Citric Acid |
| 0.00 | 6 | UCARE Polymer LR 30M (1.3%)[4] | Polyquaternium-10 |
| .00 | 7 | Lipamide MEAA[4] | Acetamide MEA |

Note:
5:1 Bio-PDO is defined as 5 parts biologically derived 1,3-propanediol with 1 part dehydrated botanical. (20% of a 1:1 extract)
[1]Rohm & Haas
[2]Henkel Procedure:
1. Combine Sequence 1 ingredients at room temperature using a slow to moderate mixing to prevent aeration until homogeneous.

2. Adjust pH to 9.2 with Sequence 2 ingredient.
3. Slowly add Sequence 3 and continue mixing until polymer is completely dispersed.
4. Add Sequence 4 ingredients slowly and mix until homogeneous.
5. Adjust pH to 5.5 with Sequence 5 ingredient.
6. Add Sequence 6 slowly and mix until homogeneous.
   Add Sequence 7 slowly and mix until homogeneous.

Example 7

All Natural Blooming Bath Oil

| Percent | Sequence | Raw Material | INCI Name |
|---|---|---|---|
| 15.96 | 1 | Lipovol ALM[5] | Sweet Almond Oil |
| 63.54 | 1 | Lipovol SES[1] | Sesame Oil |
| 5.00 | 1 | Lipolan R[1] | Lanolin Oil |
| 5.00 | 1 | Lipopeg 2-DL | PEG-4 Dilaurate |
| 10.00 | 1 | Lipocol 0–2[1] | Oleth-2 |
| 0.10 | 1 | Propylparaben | Propylparaben |
| 0.10 | 1 | Vitamin E USP-FCC[6] | Vitamin E |
| 0.10 | 2 | Arnica 5:1 BIO-PDO | Arnica Extract |
| 0.10 | 2 | Chamomile 5:1 BIO-PDO | Chamomile Extract |
| 0.10 | 2 | Comfrey 5:1 BIO-PDO | Comfrey Extract |
| q.s. | 3 | D & C Green #6 (0.5% Sol'n in BIO-PDO) | D & C Green #6 |

Note:
5:1 Bio-PDO is defined as 5 parts biologically derived 1,3-propanediol with 1 part dehydrated botanical. (20% of a 1:1 extract)
[3]Lipo Chemicals, Inc.
[4]Amerchol
[5]Lipo Chemicals, Inc.

Procedure:
1. Combine Sequence 1 ingredients under vigorous mixing and heat to 557° C. until propylparaben is completely dissolved. Cool to 30° C.
2. At 30° C., add Sequence 2 ingredients to batch and cool to 25° C.
   At 25° C., add Sequence 3 until desired shade is obtained.

Example 8

High Humectant, Aqueous Spray-On Moisturizer

| Percent | Sequence | Raw Material | INCI Name |
|---|---|---|---|
| 92.70 | 1 | Deionized Water | Water |
| 2.00 | 1 | Lipocare HA/EC[7] | Echinacin |
| 5.00 | 1 | Liponic EG-1[1] | Glycereth - 26 |
| 0.10 | 1 | Slippery Elm Bark 5:1 BIO-PDO[8] | Slippery Elm Extract |
| 0.10 | 1 | Chamomile Extract 5:1 BIO-PDO[2] | Matricaria Extract |
| 0.10 | 1 | Wild Alum Extract 5:1 BIO-PDO[2] | Cranesbill Extract |

Note:
5:1 Bio-PDO is defined as 5 parts biologically derived 1,3-propanediol with 1 part dehydrated botanical. (20% of a 1:1 extract)
[6]Roche Vitamins and Fine Chemicals
[7]Lipo Chemicals, Inc.
[8]BioBotanica/Lipo Chemicals, Inc.

Procedure:
Combine ingredients under vigorous mixing at room temperature until batch is clear and uniform.

Example 9

Extraction of Chamomile Flower Powder by Bio-PDO and Bio-PDO Ester Mixture

Esters based on biologically-derived 1,3-propanediol were synthesized, purified and characterized as it is described in U.S. Provisional Patent application 60/772,112, filed Feb. 10, 2006, incorporated herein by reference.

Biologically-derived 1,3-propanediol and 1,3-propanediol conjugate ester were used for the extraction of Chamomile flower powder (*Martricaria recutita* from Egypt, distributor—Mountain Rose Herbs, Oreg.).

The Chamomile powder was mixed with 1,3-propanediol and macerated for 30 minutes on a shaking table, then 1,3-propanediol ester was added to the mixture and the temperature was raised to 90° C. and the maceration was continued for additional 2 hours. The material was filtered through a 0.2 μm GHP membrane and the filtrate was analyzed by LC/MS and shown to contain extracted compounds.

Example 10

Extraction of Chamomile Flower Powder by Bio-PDO Ester

The biologically-derived 1,3-propanediol conjugate ester was synthesized as it is written in Example 9 and the ester (Bio-PDO bis-ethylhexanoate) was used for the extraction of Chamomile flower powder (Mountain Rose Herbs, Oreg.).

The Chamomile powder was mixed with the ester and macerated for 2, 4, 6 hours on a shaking table. The material was filtered through a 0.2 μm GHP membrane and the filtrate was analyzed by UV/VIS (UV/Vis Spectrophotometer, Varian (Australia), Model: Cary 5000) and the spectra demonstrated that the efficacy of the extracted compounds was proportional with the time used for the maceration.

Example 11

Extraction of Red Roses by Bio-PDO Ester

The biologically-derived 1,3-propanediol conjugate ester was synthesized as it is written in Example 9 and the ester (Bio-PDO bis-ethylhexanoate) was used for the extraction of dried Red Roses (*Rosa centifolia*, Mountain Rose Herbs, Oreg.).

The dried roses was mixed with the ester and macerated for 2, 4, 6 hours on a shaking table. The material was filtered through a 0.2 μm GHP membrane and the filtrate was analyzed by UV/VIS.

Example 12

Extraction of Seaweed by Bio-PDO Ester

The biologically-derived 1,3-propanediol conjugate ester was synthesized as it is written in Example 9 and the ester (Bio-PDO bis-ethylhexanoate) was used for the extraction of dried seaweed (local farmers' market).

The dried seaweed was mixed with the ester and macerated for 2, 4, 6 hours on a shaking table. The material was filtered through a 0.2 µm GHP membrane and the filtrate was analyzed by UV/VIS

Example 13

Botanical Extraction Using Bio-PDO/Methanol Mixture

Procedure: 5 g of dried Jasmine flower (*Jasminum officinale*, Mountain Rose Herbs, Oreg.) was immersed in the mixture of Bio-PDO/methanol (70%:30%) and macerated for 24 h. The material was filtered through a 0.2 µm GHP membrane and the filtrate was analyzed by LC/MS. The LC/MS spectra demonstrated the effective extraction of the active ingredients.

Example 14

Honeysuckle Flower Extraction Using Bio-PDO/Deionized Water Mixture

Procedure: 5 g of dried Honeysuckle flower (*Lonicera japonica*, origin China, distributor Mountain Rose Herbs, Oreg.) was immersed in the mixture of Bio-PDO/d.water (50%:50%) and macerated for 24 h. The material was filtered through a 0.2 µm GHP membrane and the filtrate was analyzed by LC/MS. The LC/MS spectra demonstrated the effective extraction of the active ingredients.

Example 15

Eucalyptus Leaf Extraction Using Bio-PDO/Deionized Water Mixture

Procedure: 5 g of dried Eucalyptus leaf (*Eucalyptus globulus*, origin France, distributor Mountain Rose Herbs, Oreg.) was immersed in the mixture of Bio-PDO/d.water(50%:50%) and macerated for 24 h. The material was filtered through a 0.2 µm GHP membrane and the filtrate was analyzed by LC/MS. The LC/MS spectra demonstrated the effective extraction of the active ingredients.

Example 16

Sandalwood Red Powder Extraction Using Bio-PDO/Deionized Water Mixture

Procedure: 5 g of dried Sandalwood Red Powder (*Pterocarpus santalinus*, origin Africa, distributor Mountain Rose Herbs, Oreg.) was immersed in the mixture of Bio-PDO/d.water(50%:50%) and macerated for 24 h. The material was filtered through a 0.2 µm GHP membrane and the filtrate was analyzed by LC/MS. The LC/MS spectra demonstrated the effective extraction of the active ingredients.

Comparative Example 1

Comparison Between Biologically Derived 1,3-propanediol and Propylene Glycol in Plant Material Extractions Bio-1,3-propanediol and propylene glycol were used to extract ingredients from Jasmine flower, Chamomile flower powder (*Matricaria recutita*) myrrh gum cut benzoin gum powder, and bees wax. LC-MS and GC-MS were used to analyze the extracted ingredients. Qualitative analysis confirmed that ingredients extracted using 1,3-propanediol are same as those extracted using propylene glycol. Additionally, ingredients extracted using bio-1,3-propanediol and mixtures of bio-1,3-propanediol and methanol were the same.

The major ingredients of chamomile extraction are bisabolol oxide, en-in-dicyclo ether, and Apigenin glucoside. Comparative yields of these active ingredients using 1,3-propanediol and propylene glycol (1,2-Propanediol, Aldrich) are shown below in Table 1:

TABLE 1

| Extract Product | Bio-1,3-propanediol Area | Propylene Glycol Area | % difference |
|---|---|---|---|
| Bisabolol oxide | 9217821[a] | 8760424[a] | 5.2 |
| Apigenin glucoside | 3972525[b] | 3549734[b] | 11.2 |
| en-in-dicyclo ethers | 9394370[b] | 7261956[b] | 29.2 |

[a]GC-MS analysis,
[b]LC-MS analysis

The table shows the GC-MS/LC-MS peak areas of the extracted ingredients using 1,3-propanediol and propylene glycol. Using Bio-1,3-propanediol the extraction process extracted 29.4 wt % higher en-in-cycloethers, 11.2 wt % higher apigenin glucoside, and 5.2 wt % higher bisabolol oxide as compared to the extraction using propylene glycol.

Comparative Example 2

Chamomile flower powder (5 g) was mixed with 50 g of solvent mixture (Bio-PDO/Deionized Water, ratio 1:1, and also the mixture of 1,2-Propanediol(Propylene glycol, Aldrich)/Deionized Water, ratio 1:1). The mixture was kept for agitation for 24 h. The extract was filtered and analyzed.

TABLE 2

Comparison of extraction of Chamomile using Bio-PDO and Propylene glycol

| Product | Bio-PDO/ Water Area | Propylene glycol/ Water Area | % Difference |
|---|---|---|---|
| Bisabolol oxide | 25176422 | 14409166 | 75 |
| Apigenin | 2374215 | 556691 | 326 |
| Apigenin glucoside | 658824 | 420412 | 57 |
| en-in-dicyclo ethers | 1842764 | 866635 | 113 |

The data in Table 2. show the GC-MS/LC-MS peak areas of the extracted ingredients using Bio-PDO/water and propylene glycol/water mixtures. Using Bio-PDO/water mixture 75 wt % higher Bisabolol oxide, 326 wt % higher Apigenin, 113 wt % higher en-in-cycloethers, 57 wt % higher apigenin glucoside were extracted than those extracted using propylene glycol.

Comparative Example 3

Chamomile flower powder (Mountain Rose Herb, Oreg.) (5 g) was mixed with 50 g of Bio-PDO also 5 g of Chamomile flower powder was mixed with Deionized Water. The mixture was macerated for 24 h. The extract was filtered and analyzed by LC/MS.

TABLE 3

| Comparison of extraction of Chamomile using Bio-PDO and Water | | | |
|---|---|---|---|
| Product | Bio-PDO/Area | H$_2$O/Area | % Difference |
| Apigenin | 63.32 | 125.53 | −50.4 |
| Apigenin glucoside | 134.58 | 0 | |
| en-in-dicyclo ethers | 1340.74 | 0 | |

Using deionized water apigenin glucoside and en-in-dicyclo ethers were not extracted though apigenin extraction was higher compared to that using Bio-PDO.

What is claimed:

1. A composition comprising an ester of 1,3-propanediol and an extraction product, wherein the composition is biodegradable, wherein the ester is a monomer and comprises at least 3% biobased carbon, and wherein said composition has a lower anthropogenic CO$_2$ emission profile as compared to a biodegradable composition comprising an ester of 1,3-propanediol with a bio-based carbon content of 0%.

2. The composition of claim 1, wherein the ester has at least 6% biobased carbon.

3. The composition of claim 1, wherein the ester has at least 10% biobased carbon.

4. The composition of claim 1, wherein the ester has at least 25% biobased carbon.

5. The composition of claim 1, wherein the ester has at least 50% biobased carbon.

6. The composition of claim 1, wherein the ester has at least 75% biobased carbon.

7. The composition of claim 1, wherein the ester has 100% biobased carbon.

8. The composition of claim 1, wherein the ester has the formula R1-C(=O)—O—CH2-CH2-CH2-OH, wherein R1 is a linear or branched carbon chain of a length between about 1 and about 40 carbons.

9. The composition of claim 8, wherein R1 has one or more functional groups selected from the group consisting of alkene, amide, amine, carbonyl, carboxylic acid, halide, hydroxyl groups, ether, alkyl ether, sulfate and ethersulfate.

10. The composition of claim 1, wherein the ester has the formula R1-C(=O)—O—CH2-CH2-CH2-O—C(=O)—R2, wherein R1 and R2 are linear or branched carbon chains of a length between about 1 and about 40 carbons.

11. The composition of claim 10, wherein R1 and R2 have one or more functional groups selected from the group consisting of alkene, amide, amine, carbonyl, carboxylic acid, halide, hydroxyl groups, ether, alkyl ether, sulfate and ethersulfate.

12. The composition of claim 10, wherein R1 and R2 are the same carbon chain.

13. The composition of claim 1, wherein the ester is selected from the group consisting of:
   i. propanediol distearate, monostearate and a mixture thereof;
   ii. propandiol dilaurate, monolaurate and a mixture thereof;
   iii. propanediol dioleate, monooleate and a mixture thereof;
   iv. propanediol divalerate, monovalerate and a mixture thereof;
   v. propanediol dicaprylate, monocaprylate and a mixture thereof;
   vi. propanediol dimyristate, monomyristate and a mixture thereof;
   vii. propanediol dipalmitate, monopalmitate and a mixture thereof;
   viii. propanediol dibehenate, monobehenate and a mixture thereof;
   ix. propanediol adipate;
   x. propanediol maleate;
   xi. propanediol dibenzoate;
   xii. propanediol diacetate; and
   xiii. mixtures thereof.

14. The composition of claim 13, wherein the ester is selected from the group consisting of:
   a. propanediol distearate, monostearate and a mixture thereof;
   b. propanediol dioleate, monooleate and a mixture thereof;
   c. propanediol dicaprylate, monocaprylate and a mixture thereof;
   d. propanediol dimyristate, monomyristate and a mixture thereof; and
   e. mixtures thereof.

15. The composition of claim 1, wherein the extraction product is a natural extract.

16. The composition of claim 15, wherein the natural extract is a botanical extract.

17. The composition of claim 1, wherein the extract is selected from the group consisting of botanical extracts, vegetal extracts, protein extracts, lipid extracts, marine extracts, algae extracts, milk extracts.

18. The composition of claim 1, further comprising 1,3-propanediol.

19. The composition of claim 18, wherein the 1,3-propanediol has at least 95% biobased carbon.

20. The composition of claim 19, wherein the 1,3-propanediol has 100% biobased carbon.

21. A composition comprising 1,3-propanediol and an extraction product, wherein the 1,3-propanediol is biologically derived, wherein the composition is biodegradable and has a lower anthropogenic CO$_2$ emission profile as compared to a biodegradable composition comprising 1,3-propanediol with a bio-based carbon content of 0%, and wherein the 1,3-propanediol is a monomer, and comprises at least 3% biobased carbon.

22. The composition of claim 21, wherein the 1,3-propanediol has at least 85% biobased carbon.

23. The composition of claim 21, wherein the 1,3-propanediol has at least 95% biobased carbon.

24. The composition of claim 21, wherein the 1,3-propanediol has 100% biobased carbon.

25. The composition of claim 21, wherein the extraction product is a natural extract.

26. The composition of claim 25, wherein the natural extract is a botanical extract.

27. The composition of claim 21, wherein the extract is selected from the group consisting of botanical extracts, vegetal extracts, protein extracts, marine extracts, algae extracts, milk extracts.

* * * * *